United States Patent [19]

Aumueller et al.

[11] Patent Number: 4,980,512
[45] Date of Patent: Dec. 25, 1990

[54] PREPARATION OF 2-HYDROXY-4-ALKOXYBENZOPHENONES

[75] Inventors: Alexander Aumueller, Deidesheim; Peter Neumann, Mannheim, both of Fed. Rep. of Germany

[73] Assignee: BASF Aktiengesellschaft, Ludwigshafen, Fed. Rep. of Germany

[21] Appl. No.: 421,330

[22] Filed: Oct. 13, 1989

[30] Foreign Application Priority Data

Nov. 2, 1988 [DE] Fed. Rep. of Germany ....... 3837116

[51] Int. Cl.$^5$ ............................................. C07C 45/61
[52] U.S. Cl. .................................................... 568/315
[58] Field of Search ......................................... 568/315

[56] References Cited

U.S. PATENT DOCUMENTS

| | | | |
|---|---|---|---|
| 3,584,053 | 6/1971 | Boboli et al. | 568/315 |
| 3,632,650 | 1/1972 | Hechenbleikner et al. | 568/315 |
| 3,697,599 | 10/1972 | Dalbey | 568/315 |
| 3,923,901 | 12/1975 | Battin et al. | 568/315 |
| 4,323,710 | 4/1982 | Wexler et al. | 568/315 |
| 4,453,004 | 6/1984 | Nelson | 568/315 |
| 4,613,703 | 9/1986 | Hefner | 568/315 |

FOREIGN PATENT DOCUMENTS

| | | | |
|---|---|---|---|
| 44-8656 | 4/1969 | Japan | 568/315 |
| 61-200941 | 9/1986 | Japan | 568/315 |

OTHER PUBLICATIONS

Patent Abstracts of Japan, 4048-315, 1974.
Patent Abstracts of U.S.S.R., 883,000.
Roczniki Chem. (Ann. Soc. Chim. Palonorum), 42, (1968),2, S. 243-46.
Z. obsc. Chim. 30, (1960), S. 2377-2379.
Z. obsc. Chim. 32, (1962), S. 367-369.

*Primary Examiner*—James H. Reamer
*Attorney, Agent, or Firm*—Oblon, Spivak, McClelland, Maier & Neustadt

[57] ABSTRACT

Alkoxybenzophenones of the formula (I)

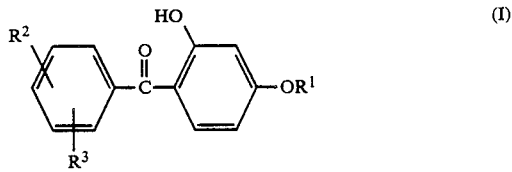

wherein $R^1$ is $C_1$-$C_4$-alkyl and $R^2$ and $R^3$ independently of one another are each hydrogen, hydroxy, $C_1$-$C_8$-alkoxy, $C_1$-$C_4$-alkyl or halogen, are prepared by reacting a benzophenone of the formula (II)

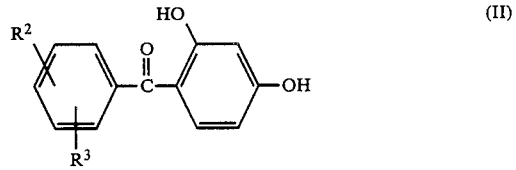

with a dialkyl sulfate of the formula (III)

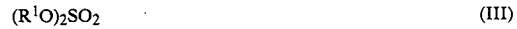

where, in the formulae, $R^1$, $R^2$ and $R^3$ have the above-mentioned meanings, by a process in which the reaction is carried out in water as the reaction medium in the presence of a base, and the dialkyl sulfate (III) is added a little at a time.

The process gives (I) in high yield and virtually free of 2,4-dialkoxybenzophenones.

16 Claims, No Drawings

PREPARATION OF 2-HYDROXY-4-ALKOXYBENZOPHENONES

2-Hydroxy-4-alkoxybenzophenones are used as light stabilizers for plastics, such as PVC, polyesters, polyacrylates, polyolefins, eg. polypropylene and polyethylene, and for coatings based on acrylates, epoxy resins or polyurethanes.

These benzophenones are also used in cosmetic articles as stabilizers for the products, and as UV absorbers in sunscreen agents.

It is an object of the present invention to provide an environmentally compatible and reliable process for the preparation of 2-hydroxy-4-alkoxybenzophenones based on the readily available 2,4-dihydroxybenzophenones.

We have found that this object is achieved with the aid of the process of the invention.

The present invention accordingly relates to a process for the preparation of alkoxybenzophenones of the formula (I)

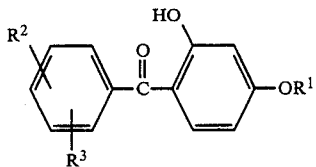

where $R^1$ is $C_1$–$C_4$-alkyl and $R^2$ and $R^3$ independently of one another are each hydrogen, hydroxyl, $C_1$–$C_8$-alkoxy, $C_1$–$C_4$-alkyl or halogen, by reacting a benzophenone of the formula (II)

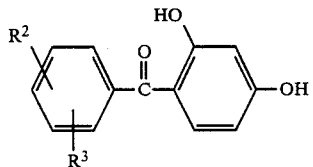

with a dialkyl sulfate of the formula (III)

$(R^1O)_2SO_2$ (III)

where, in the formulae, $R^1$, $R^2$ and $R^3$ have the above-mentioned meanings, which is characaterized in that the reaction is carried out in water as the reaction medium in the presence of a base, and the dialkyl sulfate (III) is added a little at a time.

In the process, virtually only the OH groups in the 4-position, ie. 95% or more of these groups, are alkylated. The products of the process are obtained in high purity.

The process also has the advantage that water-moist 2,4-dihydroxybenzophenones (II), as obtained in some preparation processes, can also be used directly without drying.

Specific examples of $C_1$–$C_4$-alkyl radicals $R^1$, $R^2$ and $R^3$ are methyl, ethyl, propyl and butyl. $R^1$ is preferably ethyl, in particular methyl.

$R^2$ and $R^3$ may furthermore be, for example, halogen, such as chlorine, fluorine or bromine, $C_1$–$C_8$-alkoxy, such as methoxy, ethoxy, propoxy, butoxy, pentyloxy, hexyloxy, heptyloxy, octyloxy, isooctyloxy or 2-ethylhexyloxy, hydroxyl or hydrogen, and $R^2$ and $R^3$ may be identical or different. Preferred substituents for $R^2$ and $R^3$ are methoxy, hydroxyl and hydrogen, of which hydrogen is particularly preferred.

Among the benzophenones (II), those of the formulae (IIa) to (IIc)

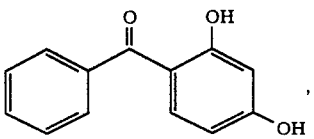

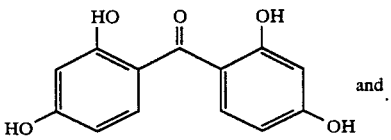

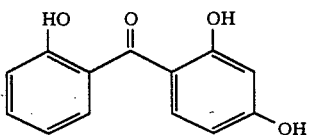

are preferred.

If the benzophenone (II) carries a second parahydroxyl group as $R^2$ or $R^3$, this group is also alkylated in the process of the invention, ie. the amounts of (III) and base must be doubled.

The process according to the invention is carried out, as a rule, by suspending or dissolving the benzophenone (II) in water in the presence of a base and then adding the dialkyl sulfate (III) a little at a time to this mixture at room temperature. After the end of the reaction, the precipitated alkylation product is isolated, for example by filtering it off under suction, and is washed with water.

If the total amount of the dialkyl sulfate is added all at once, a product of substantially lower purity is obtained in lower yield.

From 0.9 to 1.5, preferably from 1 to 1.2, moles of the dialkyl sulfate (III) are used per mole of benzophenone (II) which carries a para-hydroxyl group. An amount of 1.1 moles of (III) per mole of (II) (ie. per equivalent of para-hydroxyl group in the benzophenone) is particularly preferred.

The amounts of the base are equivalent to the amounts of (III) used, ie. one equivalent of base is used per mole of (III). In the case of sodium hydroxide solution or potassium hydroxide solution, 1 mole of these bases is used per mole of (III). If the benzophenone (II) carries two para-hydroxyl groups, twice the amounts of (III) and of the base must be used per mole of (II).

Suitable bases are the alkali metal hydroxides, the alkali metal carbonates and the alkali metal bicarbonates, magnesium hydroxide and calcium carbonate, for example sodium hydroxide, potassium hydroxide, lithium hydroxide, sodium carbonate, sodium bicarbonate, potassium carbonate and potassium bicarbonate.

Preferred bases are sodium hydroxide and potassium hydroxide in the form of their aqueous solutions.

The dialkyl sulfate (III) is added to the reaction mixture a little at a time, preferably in from 3 to 5, in particular, 4 portions.

The portions may be the same size or of different sizes. Preferably, the first 2–4 portions are roughly the same size and the last portion or the last two portions are roughly half to one fourth of the first two to four portions. The portions are added at intervals of from 5 minutes to 3 hours, preferably at intervals of from 15 to 60 minutes. The reaction is carried out at from 0° to 60° C., preferably from 15° to 50° C., particularly preferably from 20° to 40° C. It is generally complete after from 1 to 24, preferably from 2 to 7, hours, depending on the size of the batch.

At the end of the reaction, any dialkyl sulfate still present can be destroyed by adding ammonia or ammonia water. For complete precipitation of the product of the process, it may be advantageous to render the reaction mixture slightly acidic.

The products of the process are isolated in a conventional manner, for example by filtering them off under suction and washing them with water.

The crude product obtained contains, as a rule, <5, generally <2.5, % by weight of the 2,4-dialkoxy compound.

The crude product can be further purified by known methods, for example by recrystallization.

The example which follows illustrates the process.

EXAMPLE 214 g ( =1.0 mole) of 2,4-dihydroxybenzophenone were added to a mixture of 500 ml of 2 N sodium hydroxide solution and 150 ml of water at room temperature and stirring was carried out until everything had dissolved (20 minutes). Thereafter, 31.6 ml (=0.33 mole) of dimethyl sulfate were added and stirring was continued for 0.5 hour, after which a further 31.6 ml (=0.33 mole) of dimethyl sulfate were added while stirring. After 0.5 hour, a further 31.6 ml (=0.33 mole) of dimethyl sulfate were added while stirring and, after 0.5 hour, 50 ml of 2 N sodium hydroxide solution and 9.5 ml of dimethyl sulfate were added. The mixture was stirred for 1 hour at room temperature, 30 ml of concentrated ammonia solution were added and stirring was then continued for a further 0.5 hour. The precipitate which had separated out was filtered off under suction and washed with a little water to give 349 g ( 202.4 g of dry product=89% of theory) of moist 2-hydroxy-4-methoxybenzophenone, which contains 1.07% of 2,4-dimethoxybenzophenone. The moist filtration residue was recrystallized from 1,170 ml of methanol with the addition of 5 g of active carbon. After filtration under suction and drying under reduced pressure from a water pump at 50° C., 171 g (=75% of theory) of pure 2-hydroxy-4-methoxybenzophenone of melting point 62°-63° C. were obtained. According to gas chromatography, the product did not contain any dimethoxy derivative.

We claim:

1. In a process for the preparation of an alkoxybenzophenone of the formula (I)

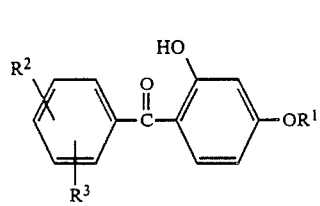

wherein $R^1$ is $C_1$-$C_4$-alkyl and $R^2$ and $R^3$ independently of one another are each hydrogen, hydroxyl, $C_1$-$C_8$-alkoxy, $C_1$-$C_4$-alkyl or halogen, by reacting a benzophenone of the formula (II)

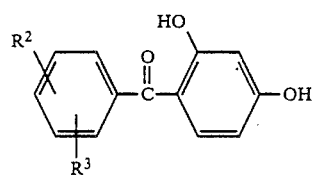

with a dialkyl sulfate of the formula (III)

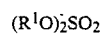

$(R^1O)_2SO_2$  (III)

where, in the formulae, $R^1$, $R^2$ and $R^3$ have the abovementioned meanings, the improvement that the reaction of (II) is carried out in water as the reaction medium in the presence of a base, and the dialkyl sulfate (III) is added in portions.

2. A process as claimed in claim 1, wherein the base used is one which is selected from the group consisting of the alkali metal hydroxides, the alkali metal carbonates, the alkali metal bicarbonates, magnesium hydroxide and calcium oxide.

3. A process as claimed in claim 1, wherein the base used is an alkali metal hydroxide 4. A process as claimed in claim 1, wherein the base used is sodium hydroxide or potassium hydroxide.

5. A process as claimed in claim 1, wherein the reaction is carried out at from 15° to 50° C.

6. A process as claimed in claim 2, wherein the reaction is carried out at from 15° to 50° C.

7. A process as claimed in claim 3, wherein the reaction is carried out at from 15° to 50° C.

8. A process as claimed in claim 4, wherein the reaction is carried out at from 15° to 50° C.

9. A process as claimed in claim 1, wherein from 0.9 to 1.5 moles of dialkyl sulfate are used per equivalent of para-hydroxyl groups.

10. A process as claimed in claim 1, wherein from 1 to 1.2 moles of dialkyl sulfate are used per equivalent of para-hydroxyl groups.

11. A process as claimed in claim 2, wherein from 1 to 1.2 moles of dialkyl sulfate are used per equivalent of para-hydroxyl groups.

12. A process as claimed in claim 3, wherein from 1 to 1.2 moles of dialkyl sulfate are used per equivalent of para-hydroxyl groups.

13. A process as claimed in claim 4, wherein from 1 to 1.2 moles of dialkyl sulfate are used per equivalent of para-hydroxyl groups.

14. A process as claimed in claim 5, wherein from 1 to 1.2 moles of dialkyl sulfate are used per equivalent of para-hydroxyl groups 15. A process as claimed in claim 7, wherein from 1 to 1.2 moles of dialkyl sulfate are used per equivalent of para-hydroxyl groups.

16. A process as claimed in claim 8, wherein from 1 to 1.2 moles of dialkyl sulfate are used per equivalent of para-hydroxyl groups

* * * * *